United States Patent [19]

Sugio et al.

[11] 4,305,879

[45] Dec. 15, 1981

[54] PROCESS FOR PRODUCING A 2-TERTIARY-ALKYL SUBSTITUTED ANTHRAQUINONES

[75] Inventors: Akitoshi Sugio, Omiya; Shizuo Togo, Chiba; Muneo Ito; Chiharu Nishizawa, both of Matsudo, all of Japan

[73] Assignee: Mitsubishi Gas Chemical Company, Inc., Tokyo, Japan

[21] Appl. No.: 124,223

[22] Filed: Feb. 25, 1980

[30] Foreign Application Priority Data

Mar. 8, 1979 [JP] Japan .................. 54-27001

[51] Int. Cl.$^3$ .............................................. C07C 50/18
[52] U.S. Cl. ................................................. 260/369
[58] Field of Search ......................................... 260/369

[56] References Cited

U.S. PATENT DOCUMENTS

| 4,002,653 | 1/1977 | Reuter et al. ............... | 260/369 |
| 4,036,860 | 7/1977 | Engelbach et al. ........... | 260/369 |
| 4,036,861 | 7/1977 | Togo et al. ................. | 260/369 |
| 4,151,182 | 4/1979 | Engelbach et al. ........... | 260/369 |
| 4,215,063 | 7/1980 | Schmitt, Jr. et al. ........ | 260/369 |

FOREIGN PATENT DOCUMENTS 2628725 12/1976 Fed. Rep. of Germany ...... 260/369
55-27001 3/1980 Japan .

*Primary Examiner*—Winston A. Douglas
*Assistant Examiner*—Raymond K. Covington
*Attorney, Agent, or Firm*—Frishauf, Holtz, Goodman & Woodward

[57] ABSTRACT

A process for producing a 2-tertiary-alkyl substituted anthraquinone, characterized by carrying out catalytic oxidation of a diphenylmethane type compound having the formula:

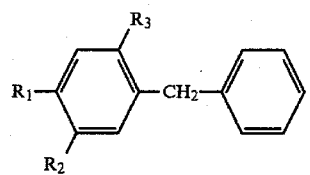

wherein $R_1$ and $R_2$ are different from each other, and independently hydrogen or tertiary-alkyl having 4 or 5 carbon atoms with the proviso that one of $R_1$ and $R_2$ is hydrogen, and $R_3$ is alkyl having 1–3 carbon atoms, in vapor phase in the presence of a catalyst containing vanadium and cerium is disclosed.

8 Claims, No Drawings

PROCESS FOR PRODUCING A 2-TERTIARY-ALKYL SUBSTITUTED ANTHRAQUINONES

BACKGROUND OF THE INVENTION

1. Object of the Invention

This invention relates to an improved process for producing a 2-tertiary-alkyl substituted anthraquinone.

2. Description of the Prior Art

A process for producing a 2-tertiary-alkyl substituted anthraquinone, characterized by carrying out catalytic oxidation of a diphenylmethane type compound having the formula:

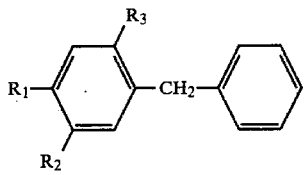

wherein $R_1$ and $R_2$ are different from each other, and independently hydrogen or tertiary-alkyl having 4 or 5 carbon atoms with the proviso that one of $R_1$ and $R_2$ is hydrogen, and $R_3$ is alkyl having 1–3 carbon atoms, in vapor phase in the presence of a catalyst containing vanadium oxide is disclosed in U.S. Pat. No. 4,036,861 dated July 19, 1977 which was assigned to the assignee of this application and which is incorporated herein.

A process for producing a 2-tertiary-alkyl substituted anthraquinone in a high yield with little or no formation of benzylbenzaldehyde is disclosed in U.S. Pat. No. 4,036,861. The catalyst disclosed in the U.S. Patent is vanadium oxide alone or combinations of vanadium oxide and other metal compounds. However, a catalyst composed of vanadium oxide alone or a mixture of vanadium oxide and other metal compounds has a relatively short life.

SUMMARY OF THE INVENTION

The inventors of this invention found that a catalyst comprising vanadium and cerium effectively accelerate the vapor phase oxidation of the diphenylmethane type compound having Formula I and has a long life. This invention is formed on the basis of this discovery.

One object of this invention is to provide a practical process for producing a 2-tertiary-alkyl substituted anthraquinone in a high yield.

This invention relates to a process for producing a 2-tertiary-alkyl substituted anthraquinone, characterized by carrying out catalytic oxidation of a diphenylmethane type compound having the formula:

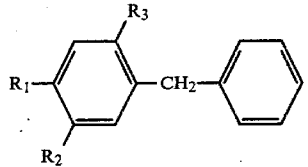

wherein $R_1$ and $R_2$ are different from each other, and independently hydrogen or tertiary-alkyl having 4 or 5 carbon atoms with the proviso that one of $R_1$ and $R_2$ is hydrogen, and $R_3$ is alkyl having 1–3 carbon atoms, in vapor phase in the presence of a catalyst comprising vanadium and cerium.

DETAILED DESCRIPTION OF THE INVENTION

It is critical that the catalyst employed in this invention contain vanadium and cerium. Both the vanadium and cerium in the catalyst are in the form of element or compound. The catalyst compound may be composed of vanadium element, cerium element and other element(s). Profitably, the catalyst comprises vanadium oxide and cerium oxide. The atomic ratio of vanadium to cerium may be in the range of from about 100:2 to about 100:60, preferably from about 100:6 to about 100:40.

The catalyst may be used in the form of molded pieces as it is or it may be conveniently used in the state in which it is carried on an inert carrier, such as electrofused alumina, spongy alumina, silicon carbide and the like. The amount of the catalyst to be carried on the inert carrier is from about 1 to about 15% by weight based on the amount of the inert carrier.

Typical examples of the diphenylmethane type compound having the formula I include 4-tert.-butyl-2-benzyltoluene, 5-tert.-butyl-2-benzyltoluene, 4-tert.-amyl-2-benzyltolunene, 5-tert.-amyl-2-benzyltoluene, 4-tert.-butyl-2-benzylethylbenzene, 5-tert.-butyl-2-benzylethylbenzene, 4-tert.-amyl-2-benzylethylbenzene, 5-tert.-amyl-2-benzylethylbenzene, 4-tert.-butyl-2-benzylcumene, 5-tert.-butyl-2-benzylcumene, 4-tert.-amyl-2-benzylcumene, 5-tert.-amyl-2-benzylcumene and the like.

The diphenylmethane type compound which is the starting material is subjected to gasification, and then the compound in a gaseous state is mixed with air. The gaseous mixture of the compound and air is passed through a reactor filled with the catalyst to oxidize the compound. The concentration of the diphenylmethane type compound having the formula I in air is not critical. Advantageously, the concentration may range from about 0.1% by mol to about 2% by mol.

The space velocity of the gasified starting material is not critical. In general, the space velocity may range from about 2,000 $Hr^{-1}$ to about 15,000 $Hr^{-1}$, preferably from about 3,000 $Hr^{-1}$ to about 10,000 $Hr^{-1}$.

The reaction temperature is not critical. The temperature may conveniently range from about 350° C. to about 450° C.

The reaction of this invention may be effected under one atmospheric pressure, a superpressure or a reduced pressure.

After the catalytic oxidation of the compound is completed, the objective anthraquinone can be separated from the resulting mixed gas by a known process. For example, the objective anthraquinone can be separated from the mixed gas by condensing the gas, or by allowing the gas to be absorbed in an organic solvent, followed by distilling the object product or by crystallizing the object product.

The present invention is further illustrated by the following Examples. However, this invention should not be limited by these examples, and the changes and modification within the spirit and scope of this invention can be effected.

COMPARATIVE EXAMPLE 1

The life of a catalyst comprising vanadium, titanium and cesium as shown in Example 2 of U.S. Pat. No. 4,036,861 was tested in this Example.

The catalyst was prepared in the following way:

In a reactor 12.87 gr. of ammonium metavanadate was suspended in 150 ml. of water. To the resulting mixture was added 25 gr. of oxalic acid dihydrate. The resulting mixture was heated to the temperature within the range of 80°-100° C. to obtain a blue solution. To the resulting solution were added 1.00 gr. of titanium tetrachloride and 0.355 gr. of cesium chloride. The resulting solution was thoroughly stirred. To the solution was added 100 gr. of electrofused alumina (average diameter 3 mm). The solution was heated and dried on a water bath to obtain a catalyst carried on the alumina. The catalyst was predried at temperature of 180° C. for 10 hours. A reactor made of stainless steel was filled with the predried catalyst, which was calcined at temperature of 500° C. for 3 hours while passing air therethrough. The atomic ratio of effective components in the resulting catalyst was V:Ti:Cs=100:5:2.

The calcined catalyst was put in a reactor made of stainless steel. The mixture of 4-tert.-amyl-2-benzyltoluene (90% by mol) and 5-tert.-amyl-2-benzyltoluene (10% by mol) was subjected to gasification and was mixed with air. The diphenylmethane type compound with concentration of 0.2% by mol was subjected to catalytic oxidation by passing it through the catalyst bed at space velocity of 3,000 Hr$^{-1}$. The reaction was continued for 130 hours. The reaction temperature were the optimum ones for the respective reaction time. The relationship between the reaction time and the yield of 2-tert.-amylanthraquinone is shown in Table 1. As is apparent from Table 1, after 10 hours, the activity of the catalyst was lowered.

TABLE 1

| Reaction time (hrs.) | Reaction Temperature (°C.) | Conversion of raw material (%) | Yield of 2-tert.-amylanthraquinone (mol %) |
|---|---|---|---|
| 10 | 394 | 95.3 | 44.4 |
| 60 | 399 | 96.0 | 40.0 |
| 130 | 404 | 97.3 | 36.1 |

EXAMPLE 1

Preparation of 2-tert.-amylanthraquinone:

To 10 gr. of vanadium pentoxide was added 150 ml of hydrochloric acid. The mixture was heated to temperature range of 60°-80° C. to obtain a dark green solution.

Cerous nitrate hexahydrate weighing 3.85 gr. was added to the solution, and the mixture was stirred to obtain a uniform solution. The solution was sprayed on 500 gr. of electrofused alumina maintained at 180° C. to carry the catalyst component on the carrier. The catalyst was put into a pipe made of stainless steel and calcined at 500° C. for 3 hours while passing air therethrough. The catalyst to be carried on alumina was obtained. The atomic ratio of effective components in the catalyst was V:Ce=100:12.

The calcined catalyst was put in a reactor made of stainless steel. The mixture of 4-tert.-butyl-2-benzyltoluene (90% by mol) and 5-tert.-butyl-2-benzyltoluene (10% by mol) which had been previously subjected to gasification and mixed with air was subjected to catalytic oxidation by passing it through the catalyst bed under the following reaction conditions.

| Reaction conditions: | |
|---|---|
| Space velocity | 3000 Hr$^{-1}$ |
| Concentration of starting material in air | 0.2% by mol |

The reaction was continued for 2,000 hours. The conversion of raw material and the yield of 2-tert.-amylanthraquinone were measured by gas chromatograph at the intervals indicated in Table 2. The results are shown in Table 2. The reaction temperatures were the ones optimum for each reaction time.

TABLE 2

| Reaction time (hrs.) | Reaction Temperature (°C.) | Conversion of raw material (%) | Yield of 2-tert.-amylanthraquinone (mol %) |
|---|---|---|---|
| 5 | 420 | 98.7 | 54.6 |
| 10 | 403 | 96.7 | 53.2 |
| 200 | 404 | 96.7 | 52.2 |
| 400 | 406 | 97.6 | 51.8 |
| 600 | 408 | 95.5 | 51.4 |
| 800 | 411 | 95.6 | 51.3 |
| 1000 | 414 | 98.5 | 52.1 |
| 1500 | 417 | 94.7 | 49.3 |
| 2000 | 420 | 95.6 | 50.7 |

EXAMPLES 2-4

Three samples of catalyst were prepared by repeating the procedure of Example 1 except that the atomic ratio of V to Ce was different from that of the catalyst obtained in Example 1.

The activity of each of the catalysts was tested by repeating the procedure of Example 1 except that a mixture of 4-tert.-amyl-2-benzyltoluene (88 mol %) and 5-tert.-amyl-benzyltoluene (12 mol %) was used as a raw material. The results are shown in Table 3.

TABLE 3

| Ex. No. | Atomic Ratio of V to Ce | Reaction Temperature (°C.) | Conversion of raw material (%) | Yield of 2-tert.-amyl-anthraquinone (%) |
|---|---|---|---|---|
| 2 | 100 to 6 | 418 | 98.7 | 51.8 |
| 3 | 100 to 40 | 420 | 99.7 | 51.0 |
| 4 | 100 to 60 | 404 | 98.0 | 52.0 |

What is claimed is:

1. A process for producing a 2-tertiary-alkyl substituted anthraquinone comprising catalytically oxidizing a diphenylmethane type compound having the formula:

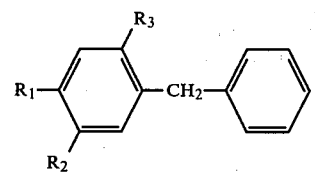

wherein $R_1$ and $R_2$ are different from each other, and independently hydrogen or tertiary-alkyl having 4 or 5 carbon atoms with the proviso that one of $R_1$ and $R_2$ is hydrogen, and $R_3$ is alkyl having 1-3 carbon atoms, said catalytic oxidation being carried out in the presence of oxygen or air in the vapor phase in the presence of a catalyst containing vanadium and cerium.

2. The process as defined in claim 1 wherein the catalyst contains vanadium oxide and cerium oxide.

3. The process as defined in claim 1 wherein the atomic ratio of vanadium to cerium is in the range of about 100:2 to 100:60.

4. The process as defined in claim 1 wherein the catalyst is carried on an inert carrier.

5. The process as defined in claim 4 wherein the carrier is selected from the group consisting of electrofused alumina, spongy alumina and silicon carbide.

6. The process as defined in any one of claims 1, 2, 4 or 5 wherein the atomic ratio of vanadium to cerium is in the range of about 100:6 to 100:40.

7. The process as defined in claim 6 wherein said catalytic oxidation is carried out in the presence of air.

8. The process as defined in claim 1, 2 or 3 wherein said catalytic oxidation is carried out in the presence of air.

* * * * *